March 28, 1961 E. S. BOERNER Plant Pat. 2,039
ROSE PLANT
Filed June 20, 1960
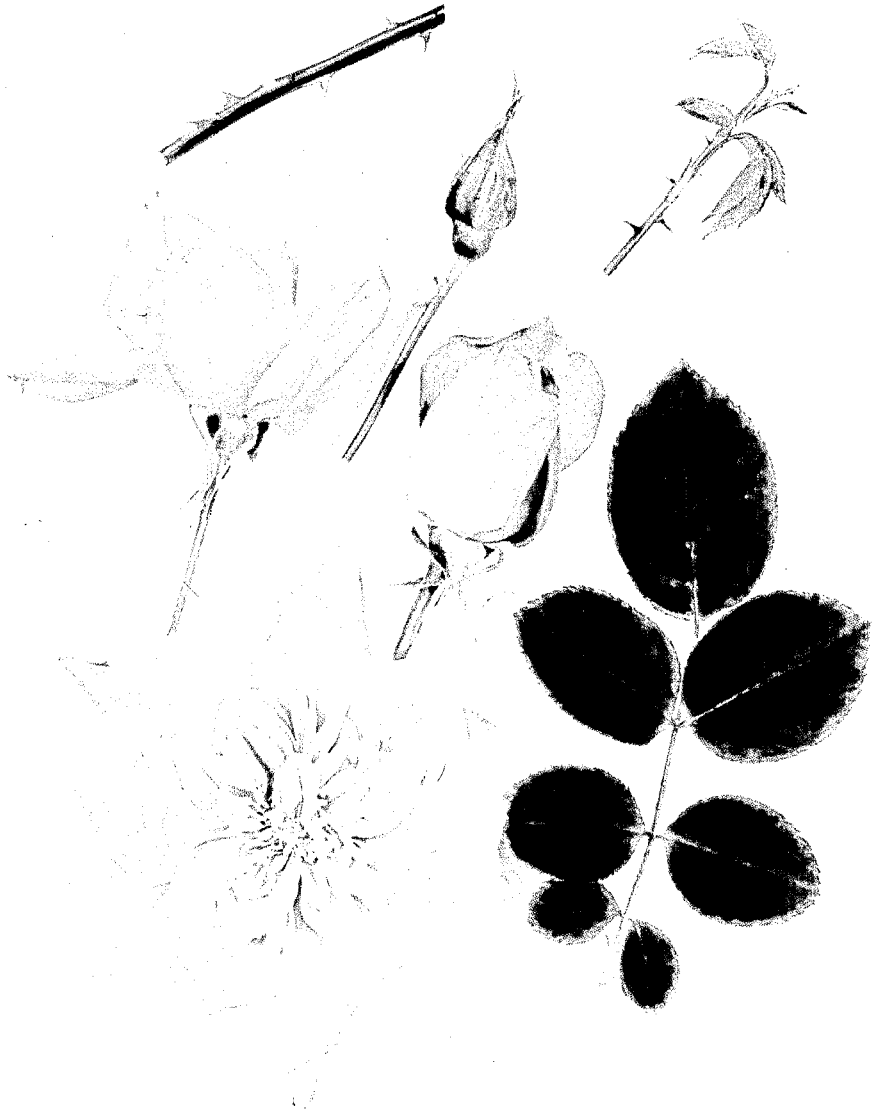
Inventor.
E. S. Boerner
By: Robb & Robb
Attorneys United States Patent Office Plant Pat. 2,039
Patented Mar. 28, 1961

2,039

ROSE PLANT

Eugene S. Boerner, Newark, N.Y., assignor to Jackson & Perkins Company, Newark, N.Y., a corporation of New York Filed June 20, 1960, Ser. No. 37,538

1 Claim. (Cl. 47—61)

The present invention relates to a new and distinct variety of rose plant, of the hybrid tea class, which was originated by me by crossing the variety "Golden Masterpiece" (Plant Patent No. 1,284) with an unnamed and unpatented seedling of "Grey Pearl" (Plant Patent No. 680).

The primary objective of this breeding was to produce a new hybrid tea rose variety which bears flowers of an attractive lavender shade. This objective was fully achieved, along with other desirable improvements, as evidenced by the following unique combination of characteristics which are outstanding in the new variety and which distinguish it from its parents, as well as from all other varieties of which I am aware:

(1) Full and vigorous habits of plant growth;
(2) A free blooming habit;
(3) Large bloom size;
(4) A distinctive bud color corresponding to light Rosolane Purple, lightly overcast with Tyrian Pink; and
(5) A distinctive open flower color corresponding to Rosolane Pink, lightly overcast with Pale Rosolane Purple in the center of the flower, and with Rosolane Purple on the outer petals.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—"Golden Masterpiece."
*Pollen parent.*—An unnamed seedling of "Grey Pearl."

Classification:
*Botanic.*—Hybrid tea.
*Commercial.*—Hybrid tea.

*Flower*

(Observations made from specimens grown outdoors at Newark, New York, in the early afternoon during the early part of August.)

Blooming habit: Recurrent—continuous.

Bud:
*Size.*—Large.
*Form.*—Ovoid; is not affected by wet or hot weather.
*Color.*—When sepals first divide—Rosolane Purple, Plate 26. When petals begin to unfurl—Rosolane Purple, Plate 26, lightly overcast with Light Rosolane Purple, Plate 26. When half-blown: inside of petals—Light Rosolane Purple, Plate 26, lightly overcast with Tyrian Pink, Plate 12; reverse of petals—Rosolane Purple, Plate 26, lightly overcast with Pale Rosolane Purple, Plate 26.
*Sepals.*—Slightly branched; curl back when petals begin to unfurl. Color: inside—Deep Chrysolite Green, Plate 31; outside—Light Cress Green, Plate 31.
*Calyx.*—Color—Light Cress Green, Plate 31. Shape—apple. Size—broad. Aspect—smooth. Odor when rubbed—none.
*Peduncle.* — Length — medium. Aspect — rough. strength—erect; slender. Color—Biscay Green, Plate 17.
*Opening.*—Opens up well; is not affected by adverse weather conditions.

Bloom:
*Size.*—Large. Average size when fully expanded—from 5 inches to 5½ inches.
*Borne.*—Singly and several together; very free blooming.
*Stems.*—Long; strong.
*Form (when first open).*—Open. Permanence—retains its form to the end, but outer petals curl back.
*Petalage.*—Very double (many petals and stamens hidden). Number of petals under normal conditions—from 65 to 70.
*Color.*—Center of flower—Rosolane Pink, Plate 26, lightly overcast with Pale Rosolane Purple, Plate 26. Outer petals—Rosolane Purple, Plate 26. Base of petals (aiglet)—Barium Yellow, Plate 16. Inside of petals—Rosolane Pink, Plate 26, lightly overcast with Pale Rosolane Purple, Plate 26. Reverse of petals—Cameo Pink, Plate 26, lightly overcast with Rosolane Pink, Plate 26. General tonality from a distance—Rosolane Pink, Plate 26, lightly overcast with Pale Rosolane Purple, Plate 26.
*Discoloration.*—General tonality at end of first day—Rosolane Pink, Plate 26, lightly overcast with Pale Rosolane Purple, Plate 26. Second day—Rosolane Pink, Plate 26, lightly overcast with Pale Rosolane Purple, Plate 26. Third day—Rosolane Pink, Plate 26.

Petals:
*Texture.*—Thick; is not affected by wet or hot weather.
*Appearance.*—Inside—satiny. Outside—shiny.
*Form.*—Oval-pointed.
*Arrangement.*—Imbricated (regularly arranged shingle-like).
*Petaloids in center.*—Many; large.
*Persistence.*—Drop off cleanly.
*Fragrance.*—Moderate. Nature—fruity (russet apple).
*Lasting quality.*—On the plant—long. As cut flower—long.

*Genital organs*

Stamens, anthers: Medium size; many; regularly arranged around styles. Color—Apricot Yellow, Plate 4.
Stamens, filaments (threads): Medium length. Color—Carmine, Plate 1.
Pollen: Color—Maize Yellow, Plate 4.
Styles: Bunched; uneven length; medium length; thin.
Stigmas: Color—Warm Buff, Plate 15.
Ovaries: All enclosed in calyx.
Hips: None.
Seeds: None.

*Plant*

Form: Bush; very full.
Growth: Vigorous; upright.
Foliage: Compound of 3 to 7 leaflets.
*Size.*—Large.
*Quantity.*—Normal.
*Color.*—New foliage: upper side—Oxblood Red, Plate 1; under side—Courage Green, Plate 17, lightly overcast with Oxblood Red, Plate 1. Old foliage: upper side—Dark Cress Green, Plate 31; underside—Light Cress Green, Plate 31, with outer edge lightly overcast with Oxblood Red, Plate 1.
*Shape.*—Oval pointed.
*Texture.*—Upper side—leathery. Under side—smooth.
*Ribs and veins.*—Ordinary.
*Edge.*—Serrated (saw-toothed).
*Serration.*—Both double and single; small.
*Leaf stem.*—Color—Biscay Green, Plate 17. Under side—prickly.
*Stipules.*—Medium length; small.
Wood:
*New wood.*—Color—Buffy Citrine, Plate 16. Bark—smooth.

*Old Wood.*—Color—Cress Green, Plate 31. Bark—smooth.
Thorns:
*Thorns.*—Quantity: on main stalks from base—ordinary; on laterals from stalk—ordinary. Form—narrow base; short; hooked downward. Color (when young)—Eugenia Red, Plate 13. Position—irregular.
*Prickles.*—Quantity: on main stalks—none; on laterals—none.
*Short needles.*—Quantity: on main stalks—none; on laterals—none.

I claim:

A new and distinct variety of rose plant of the hybrid tea class, substantially as herein shown and described, characterized particularly as to novelty by the unique combination of full and vigorous habits of plant growth, a free blooming-habit, large bloom size, a distinctive bud color corresponding to light Rosolane Purple, lightly overcast with Tyrian Pink, and a distinctive open flower color corresponding to Rosolane Pink, lightly overcast with Pale Rosolane Purple in the center of the flower, and with Rosolane Purple on their outer petals.

No references cited.